United States Patent
Hosokawa et al.

(10) Patent No.: US 7,967,518 B2
(45) Date of Patent: Jun. 28, 2011

(54) STICK-SHAPED SOLID COSMETICS AND METHOD FOR PRODUCING THE SAME

(75) Inventors: Kinya Hosokawa, Yokohama (JP);
Toshimitsu Kuroiwa, Kamakura (JP);
Masami Abe, Kamakura (JP); Takashi Minami, Yokohama (JP); Sadaki Takata, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 928 days.

(21) Appl. No.: 11/911,158

(22) PCT Filed: Apr. 10, 2006

(86) PCT No.: PCT/JP2006/307548
§ 371 (c)(1),
(2), (4) Date: Oct. 12, 2007

(87) PCT Pub. No.: WO2006/109763
PCT Pub. Date: Oct. 19, 2006

(65) Prior Publication Data
US 2008/0213028 A1 Sep. 4, 2008

(30) Foreign Application Priority Data
Apr. 11, 2005 (JP) ................. 2005-113172

(51) Int. Cl.
*A45D 40/20* (2006.01)
(52) U.S. Cl. ......................... 401/88; 424/401
(58) Field of Classification Search ............ 401/49, 401/72, 78, 88; 424/401, 63, 64
See application file for complete search history.

(56) References Cited

U.S. PATENT DOCUMENTS

| | | | |
|---|---|---|---|
| 3,192,933 A | 7/1965 | Prince | |
| 3,279,999 A | 10/1966 | Harrison et al. | |
| 3,453,056 A | 7/1969 | Motsavage et al. | |
| 4,291,018 A | 9/1981 | Oeda et al. | |
| 6,503,516 B1 * | 1/2003 | Van Liew et al. | 424/401 |
| 6,969,208 B2 * | 11/2005 | Shinya | 401/87 |
| 2005/0260146 A1 | 11/2005 | Blin | |

OTHER PUBLICATIONS

International Search Report for PCT/JP2006/307548, mailed Jul. 18, 2006, four pages.
Japanese Patent Abstract Publication No. 2005-168848, published Dec. 11, 2003, one page.
Japanese Patent Abstract Publication No. 2002-191431 published Jul. 9, 2002, one page.
Japanese Patent Abstract Publication No. 2004-224707 published Aug. 12, 2004, one page.
Japanese Patent Abstract Publication No. 2004-339132 published Dec. 2, 2004, one page.

* cited by examiner

*Primary Examiner* — David J Walczak
(74) *Attorney, Agent, or Firm* — Rankin, Hill & Clark LLP

(57) ABSTRACT

Stick-shaped solid cosmetic 10 comprises a wax with a melting point of 45° C. or higher and liquid oil, wherein the hardness of top portion 16 is 0.07 N to 0.38 N and the hardness of boundary portion 20, which is a border between a retained portion in inner holder 12 and a portion outside of the inner holder 12, is 0.03 N to 0.31 N higher than the hardness of the top portion, and wherein the hardness gradually increases from the top portion 16 to the boundary portion 20. Thus, the stick-shaped solid cosmetic 10 has smooth spreadability and excellent product strength.

8 Claims, 5 Drawing Sheets

STICK-SHAPED SOLID COSMETICS AND METHOD FOR PRODUCING THE SAME

RELATED APPLICATIONS

This application claims the priority of Japanese Patent Application No. 2005-113172 filed on Apr. 11, 2005, which is incorporated herein by reference.

FIELD OF THE INVENTION

The present invention relates to stick-shaped solid cosmetics, and in particular, relates to the improvement of product strength.

BACKGROUND OF THE INVENTION

The product requirements for lipstick, which is one of stick-shaped solid cosmetics, are that it does not break or soften during storage, carrying, or use and that it can smoothly stick on the lips and impart a gloss.

However, in order to achieve shape-retaining ability that is necessary for lipstick, the hardness should be increased to a certain level. If the hardness is too high, the spreadability is poor during application and the gloss of an applied film is low.

Thus, it is difficult to simultaneously satisfy the requirements of the shape-retaining ability and a comfortable feeling in use, and this issue presents a big challenge.

Particularly, in recent years, lipstick that provides a smooth feeling in use is preferred. Therefore, soft lipstick is regularly produced, and it sometimes breaks during use especially in the hot summer, presenting a problem.

In order to prepare lipstick with smooth spreadability and high breakage strength, some attempts to blend various components have been made. For example, the blending technology of candelilla wax and hydrogenated jojoba ester is disclosed in patent literature 1. In patent literature 2, the blending technology of ethylene-propylene copolymer and a ditrimethylolpropane derivative containing a hydroxyl group is disclosed.

In patent literature 3, the container is designed so that lipstick will not easily break; in the disclosed technology, the lipstick supporting part is formed in a coil spring shape.

In patent literature 4, a stick-shaped cosmetic is disclosed in that a wax composition with high hardness is filled and solidified at the bottom of the inner holder, and the bottom portion of lipstick is connected with the wax composition at the top of the inner holder so that the lipstick is retained well by their mixing.

Patent literature 1: Japanese Unexamined Patent Publication No. 2004-224707
Patent literature 2: Japanese Unexamined Patent Publication No. 2004-339132
Patent literature 3: Japanese Unexamined Patent Publication No. 2002-191431
Patent literature 4: Japanese Unexamined Patent Publication No. 2005-168848

DISCLOSURE OF THE INVENTION

Problem to be Solved by the Invention

However, the formulation is limited in the blending method of specific components as shown in patent literatures 1 and 2. In the method of designing a container, as shown in patent literature 3, the structure becomes too complicated and the productivity is poor. In the method described in patent literature 4, it is possible to prevent lipstick from falling out of the inner holder when the container is dropped. However, it will not prevent breakage of the lipstick during its use; thus there is a limit in softening the lipstick itself. Thus, the above problems could not exactly be solved by any of the above technologies.

The present invention was made in view of the above-described problems of the past technologies, and the object is to provide stick-shaped solid cosmetics with smooth spreadability and excellent product strength.

Means to Solve the Problem

In view of the foregoing, the present inventors have diligently studied to solve the above-problems. As a result, the present inventors have found that it is possible to obtain a desired stick-shaped solid cosmetic by making the hardness of the top end of the stick-shaped solid cosmetic softer than that of the bottom end, thus leading to completion of the present invention.

The stick-shaped solid cosmetic of the present invention is characterized by comprising a wax with a melting point of 45° C. or higher and a liquid oil component, and wherein hardness of a top portion is 0.07 N to 0.38 N, and hardness of a boundary portion, which is a border between a retained portion in the inner holder and a portion outside of the inner holder, is 0.03 N to 0.31 N higher than the hardness of the top portion at least in the vicinity of a central axis of the stick-shaped solid cosmetic.

In the above-described stick-shaped solid cosmetic, it is desirable that, at least in the vicinity of the central axis of the stick-shaped solid cosmetic, the hardness gradually increases from the top portion to the boundary portion.

In the above-described stick-shaped solid cosmetic, it is desirable that, at least in the vicinity of the central axis of the stick-shaped solid cosmetic, hardness of the middle portion, which is located between the top portion and the boundary portion, is not less than the hardness of the top portion and not more than the hardness of the boundary portion, and hardness difference between the top portion and the middle portion is 30% to 67% of hardness difference between the top portion and the boundary portion.

In the above-described stick-shaped solid cosmetic, it is desirable that hardness at a location 8 mm from the boundary portion to a direction of the top portion is 0.15 N or higher, and is higher not less than 0.1 N than the hardness of the top portion.

The method of producing a stick-shaped solid cosmetic of the present invention comprises: a heating-melting step; a filling step; and a cooling-solidification step. In the heating-melting step, Phase A, which comprises a liquid oil component and a wax with a melting point of 45° C. or higher, and hardness of which is 0.05 N to 0.35 N; and Phase B, which is one or more than one phase comprising a liquid oil component and a wax with a melting point of 45° C. or higher, and hardness of which is 0.05 N to 0.50 N higher than that of Phase A, are separately heated and melted. In the filling step, the heat-melted Phase A and the heat-melted Phase B are filled into a mold while being mixed. In the cooling-solidification step, the mixture filled into the mold is solidified by cooling. In the filling step, the filling of Phase A into the mold is completed sooner than the filling of Phase B into the mold. Thus, a stick-shaped solid cosmetic in which hardness gradually increases from the top portion to the bottom portion is produced.

In the above-described method of producing a stick-shaped solid cosmetic, it is desirable that a volume ratio of Phase B to Phase A is 0.2 or higher.

In the present invention, the "normal temperature" means 25° C.

In the present invention, the "hardness" is defined by the maximum value (N) of the stress values (N) that are measured, under the conditions of the penetrator diameter of 1 mm and the penetration velocity of 2 cm/min, for a sample at 25° C. to the penetration depth of 3 mm.

In the present invention, the "hardness of the top portion" means the hardness at the position 10 mm from the tip of the stick-shaped solid cosmetic to the direction of the boundary portion.

In the present invention, the "hardness of the middle portion" means the hardness at the location of the ½ length, from the top portion, of the axial length from the top portion to the boundary portion.

EFFECT OF THE INVENTION

The stick-shaped solid cosmetic of the present invention has smooth spreadability and excellent product strength because the hardness of the top portion is softer than the hardness of the boundary portion.

Figure 1:
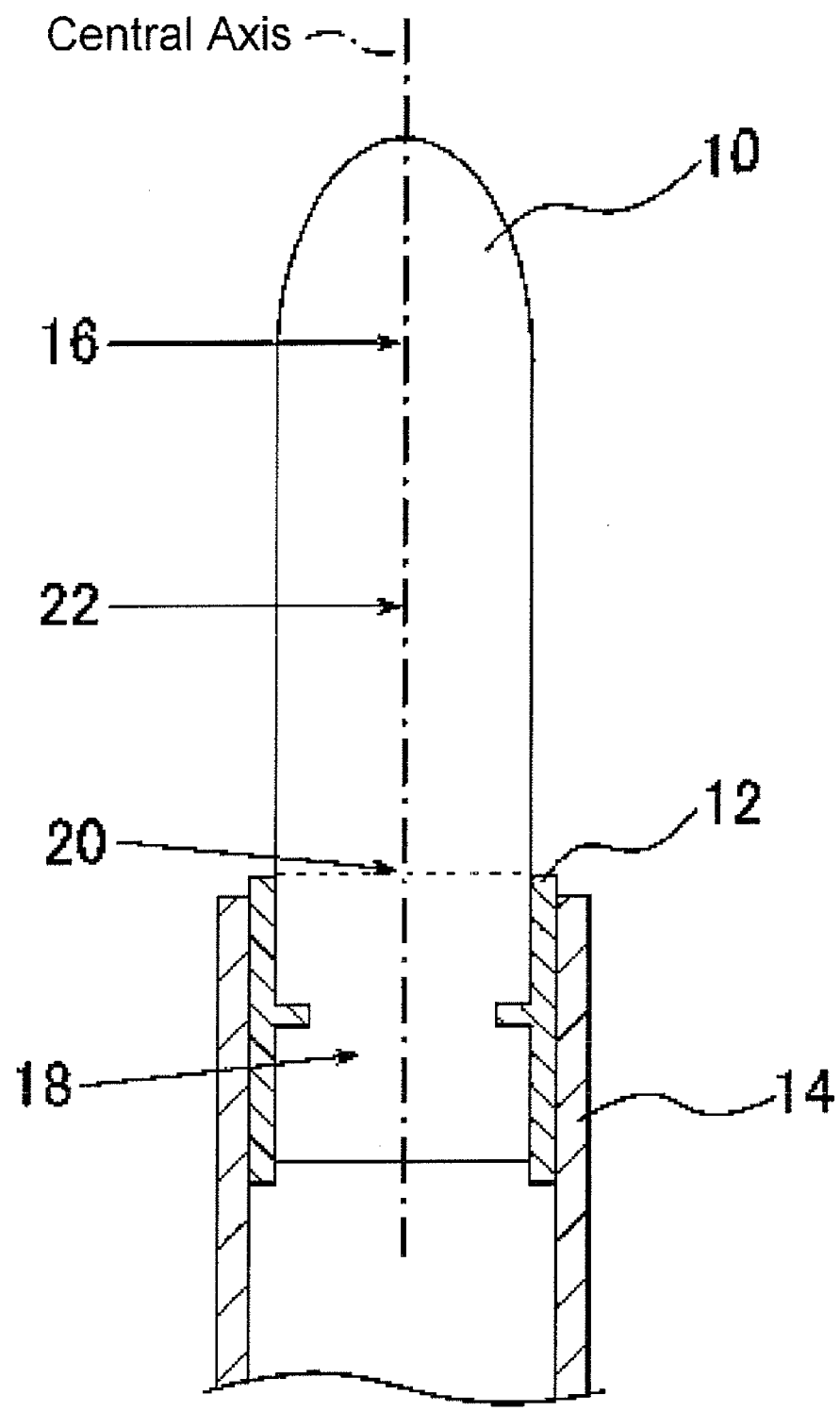
FIG. 1 is a schematic view of a stick-shaped solid cosmetic of an embodiment of the present invention.

DESCRIPTION OF REFERENCE NUMBERS 10 stick-shaped solid cosmetic
12 inner holder
14 main container
16 top portion
18 bottom portion
20 boundary portion
22 middle portion

BEST MODE FOR CARRYING OUT THE INVENTION

In the following, the preferable mode for carrying out the present invention is described.

FIG. 1 is a cross-sectional view that illustrates a stick-shaped solid cosmetic of an embodiment of the present invention. The bottom portion 18 of the stick-shaped solid cosmetic 10 is retained in the tubular inner holder 12. The inner holder 12 is stored in the tubular main container 14 so that it is axially movable. Thus, it is possible to let out and let in the stick-shaped solid cosmetic 10 from the main container 14. As the moving mechanism of the inner holder 12 in the main container 14, there are known mechanisms, for example, a mechanism in which spiral grooves are installed on the inner wall of the main container. The constitution of the main container 14 and the inner holder 12 is not limited to the shown example, and other constitution may be used.

The stick-shaped solid cosmetic 10 comprises a wax with a melting point of 45° C. or higher and a liquid oil component, and the hardness of the top portion is softer than the hardness of the boundary portion, which is the border between the bottom portion 18 in the inner holder 12 and the portion outside of the inner holder 12. Specifically, the hardness of the top portion 16 is 0.07 N to 0.38 N, and the hardness of the boundary portion 20 is 0.03 N to 0.31 N higher than the hardness of the top portion 16. Thus, in the constitution of the stick-shaped solid cosmetic 10 of the present embodiment, the top portion 16 is soft and the boundary portion 20 is hard; thus it has high breakage strength while maintaining smooth spreadability during use.

Figure 2:
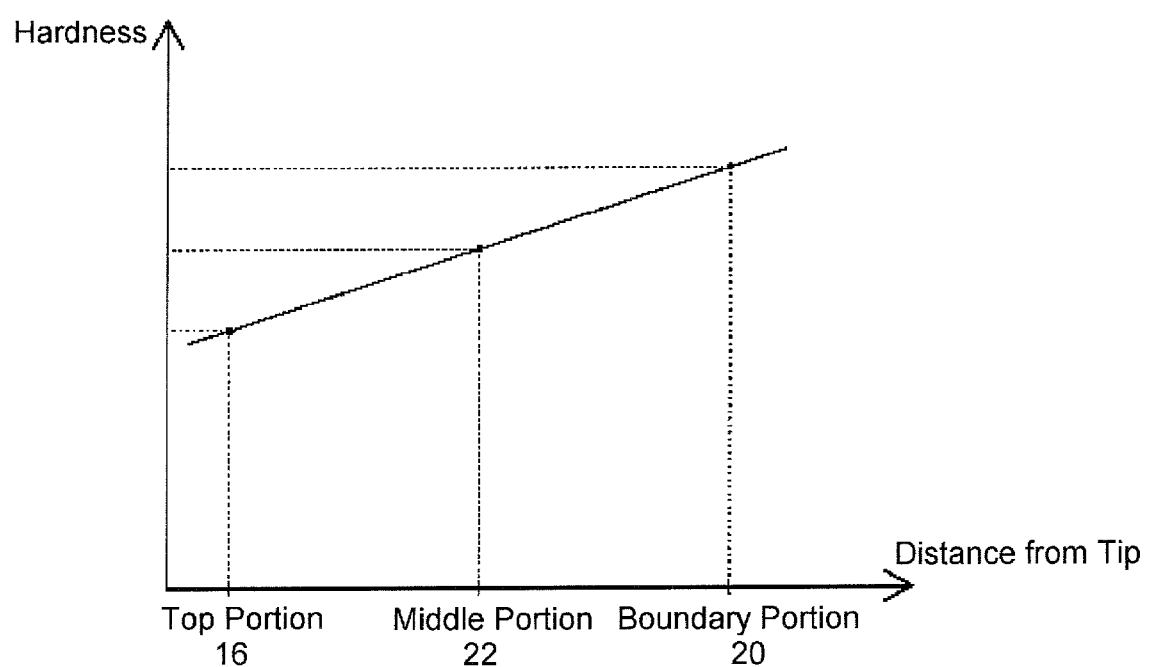
FIG. 2 is a view schematically showing the relationship between the axial position of a stick-shaped solid cosmetic of an embodiment of the present invention and the hardness.

Generally, a stick-shaped solid cosmetic often breaks during use in the vicinity of the open end (section to let out the stick-shaped solid cosmetic) of the main container 14. Therefore, as shown schematically in FIG. 2, it is desirable that the hardness of the stick-shaped solid cosmetic 10 gradually increases from the top portion 16 to the direction of the boundary portion 20. That is because the hardness in the vicinity of the open end of the main container 14 is always higher than the hardness of the top portion 16 at any let-out length of the stick-shaped solid cosmetic 10 from the main container 14. In addition, the hardness in the vicinity of the open end itself becomes high in proportion to the let-out length; as a result, it is not easily breakable. If there is a section where the hardness drastically changes, the section may become easily breakable. When that section shows up on the surface, a negative effect may be exerted to the feeling in use and to the appearance.

Thus, it is desirable that the hardness of the middle portion 22 located between the top portion 16 and the boundary portion 20 is approximately in the middle of the hardness of the top portion 16 and the hardness of the boundary portion 20. Specifically, it is desirable that the hardness difference between the top portion 16 and the middle portion 22 is 30% to 67% of the hardness difference between the top portion 16 and the boundary portion 20.

The hardness of the boundary portion 20 and the hardness of the middle portion 22 need to be higher than the hardness of the top portion 16 at least in the vicinity of the central axis of the stick-shaped solid cosmetic 10. In other words, the hardness of the boundary portion 20 and the hardness of the middle portion 22 need not to be higher than the hardness of the top portion 16 in the entire cross section perpendicular to the central axis, and they need to be higher than the hardness of the top portion only at the cross section in the vicinity of the central axis. It is desirable that this region with high hardness is 30% or more of the total cross-sectional area, of the middle portion, that is perpendicular to the central axis, and more preferably 50% or higher. It is also desirable that this region with high hardness is 40% or more of the total cross-sectional area, of the boundary portion, that is perpendicular to the central axis, and more preferably 60% or higher.

Generally speaking, a stick-shaped solid cosmetic often breaks at a position in the vicinity of the retained portion in the inner holder. Therefore, it is desirable that the hardness at the position 8 mm from the boundary portion is 0.15 N or higher and that the hardness is higher not less than 0.1 N than the hardness of the top portion.

Production Method

The method of producing a stick-shaped solid cosmetic for the embodiment of the present invention comprises a heating-melting step, a filling step, and a cooling-solidification step.

In the heating-melting step, Phase A, which comprises a liquid oil component and a wax with a melting point of 45° C. or higher, and the hardness of which is 0.05 N to 0.35 N; and Phase B, which is one or more than one phase comprising a liquid oil component and a wax with a melting point of 45° C. or higher, and the hardness of which is 0.05 N to 0.50 N higher than that of Phase A, are separately heated and melted.

Figure 3A:
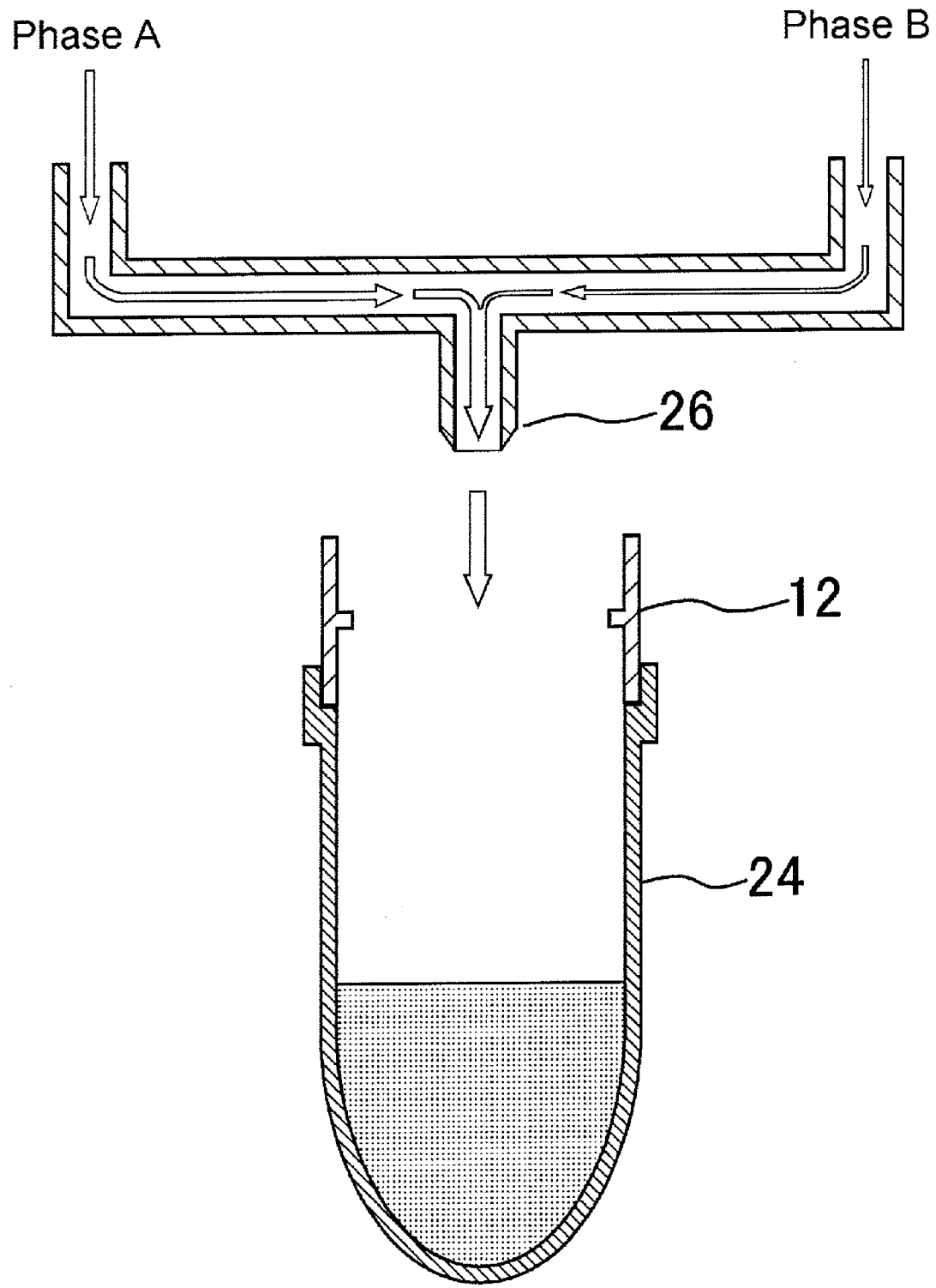
FIG. 3A is a view illustrating a method of producing a stick-shaped solid cosmetic of an embodiment of the present invention.

In the filling step, the heat-melted Phase A and the heat-melted Phase B are filled into a mold while being mixed. Thus, as shown schematically in FIG. 3A and FIG. 3B, the top portion side of the inner holder 12 is beforehand covered with the mold 24. Then, heat-melted Phase A and heat-melted Phase B are filled, while being mixed, through the filling spout 26 into the mold 24 from the opposite side of the inner holder 12 (side that is not covered by the mold 24).

Figure 3B:
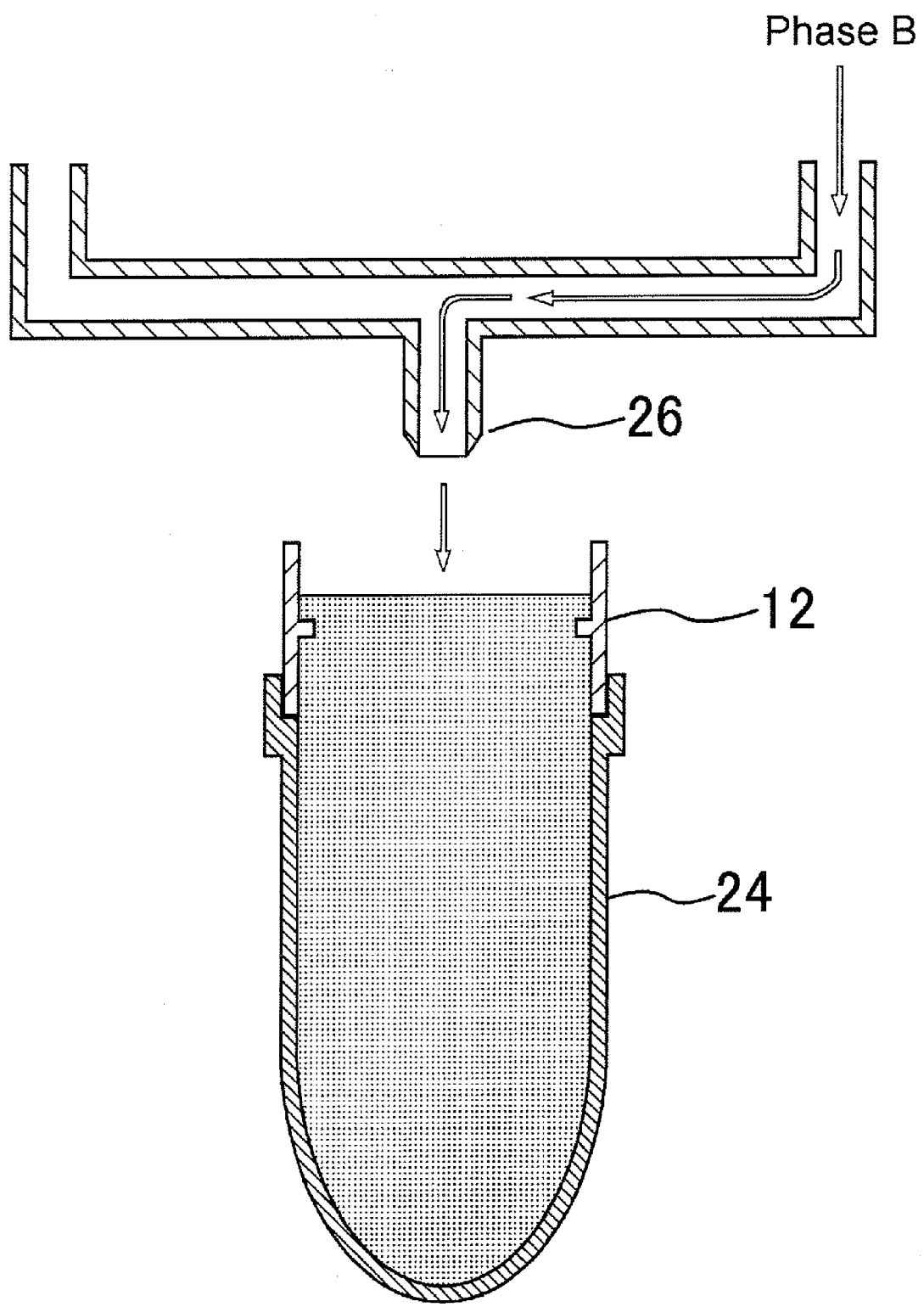
FIG. 3B is a view illustrating a method of producing a stick-shaped solid cosmetic of an embodiment of the present invention.

In this filling step into the mold 24, the filling speed of Phase B is adjusted slower than the filling speed of Phase A. Thus, as shown in FIG. 3B, the filling of Phase A into the mold 24 is completed sooner than the filling of Phase B into the mold 24. In addition, the starting time of Phase B filling into the mold 24 may be delayed than the starting time of Phase A filling into the mold 24.

In the cooling-solidification step, the mixture filled into the mold, as described above, is solidified by cooling. After cooling-solidification, a stick-shaped solid cosmetic can be produced by removing the mold 24.

In the filling step, as described above, melted Phase A and melted Phase B are filled into the mold 24 while being mixed, and the Phase A filling into the mold 24 is completed sooner than the Phase B filling. As a result, the concentration of Phase B gradually increases from the bottom to the top of the mold 24 because of the diffusion of Phase B. Thus, the hardness of the molded stick-shaped solid cosmetic gradually increases from the top portion to the bottom portion because the hardness of Phase B is higher than that of Phase A.

Here, the hardness of Phase A is preferably 0.05 N to 0.35 N, and more preferably 0.10 N to 0.25 N. If the hardness is less than 0.05 N, the stick-shaped solid cosmetics may break during use. If the hardness is more than 0.25 N, a smooth feeling in use may not be achieved.

The hardness difference between Phase A and Phase B is preferably 0.05 N to 0.50 N, and more preferably 0.10 N to 0.40 N. If the hardness difference is less than 0.05 N, the satisfactory effect of the present invention may not be obtained. If the hardness difference is more than 0.50 N, the mixing state of Phase A and Phase B becomes poor.

In addition, the volume ratio of Phase B to Phase A is preferably 0.2 or higher, and more preferably 0.4 to 1.5. If the volume ratio is less than 0.2, it may become easily breakable. If the volume ratio is more than 1.5, a smooth feeling in use may not be achieved.

In the example shown above, a heat-melted composition is directly filled into the inner holder, cooled, and solidified. Instead, a stick-shaped solid cosmetic that has been beforehand molded and solidified in the mold may be inserted into the inner holder. However, the above-described direct filling is preferable because the production process can be simplified and the cost can be reduced.

Figure 4:
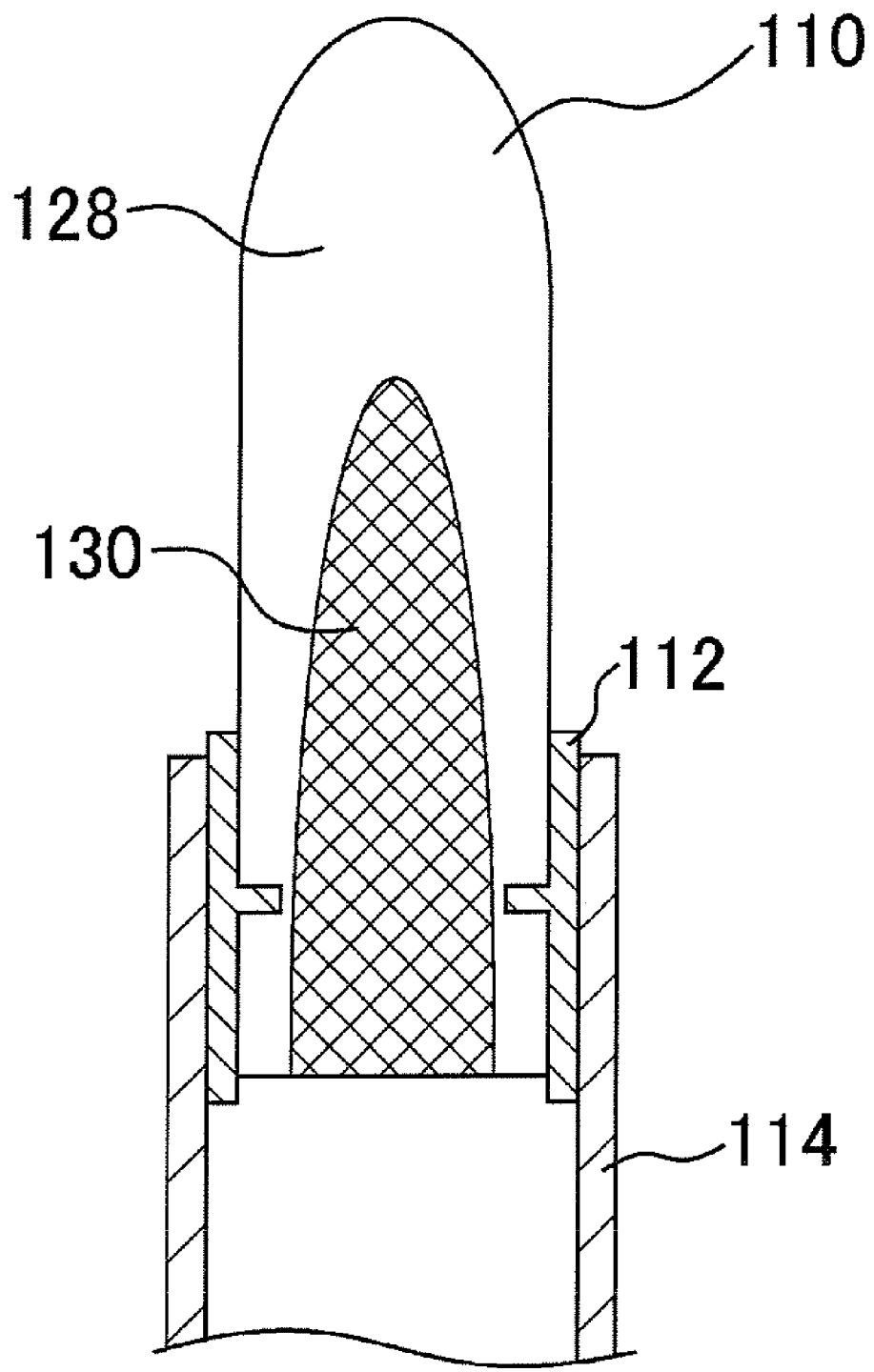
FIG. 4 is a view showing a variant example of the embodiment described in FIG. 1.

FIG. 4 is a cross-sectional view of a variant example of the above-described embodiment. The parts that correspond to those of FIG. 1 are designated by the numbers obtained by adding 100 to the numbers in FIG. 1, and detailed explanations were omitted. The stick-shaped solid cosmetic 110 shown in FIG. 3 is constituted by two phases: the low-hardness phase 128 and the high-hardness phase 130, which has a higher hardness than the low-hardness phase 128. The low-hardness phase 128 is located in the peripheral section, and the high-hardness phase 130 is located in the inner core section. In other words, the vicinity of the central axis of the middle portion and the vicinity of the central axis of the boundary portion are constituted by the high-hardness phase 130, and the peripheral section of the middle portion, the peripheral section of the boundary portion, and the top portion are constituted by the low-hardness phase. It is desirable that the hardness of the low-hardness phase is 0.05 N to 0.35 N and that the hardness of the high-hardness phase is 0.05 N to 0.50 N higher than the hardness of the low-hardness phase. Here, the case in which a stick-shaped solid cosmetic is constituted by the two phases, namely, the low-hardness phase 128 and the high-hardness phase 130, was shown. However, the low-hardness phase 128 and the high-hardness phase 130 may be constituted by two phases or more with different hardness, and they may be arranged in the order of increasing hardness from the peripheral section to the inner central section.

In this variant example, the hardness drastically changes at the border between the low-hardness phase 128 and the high-hardness phase 130. Therefore, when the stick-shaped solid cosmetic is worn down, the high-hardness phase 130 shows up on the surface layer and a negative effect may be exerted to the feeling in use and to the appearance. Therefore, it is desirable that the hardness gently changes from the tip to the boundary portion as is the case for the stick-shaped solid cosmetic in the embodiment shown in FIG. 1.

In the present invention, examples of waxes with a melting point of 45° C. or higher include ceresin, ozocerite, paraffin wax, polyethylene wax, microcrystalline wax, beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, and POE hydrogenated lanolin alcohol ether. One or more kind of these waxes can be used. An amount of waxes with a melting point of 45° C. or higher, which is not particularly limited to, is usually 3 mass % to 25 mass % of the entire cosmetic.

In the present invention, examples of liquid oils include liquid fats and oils such as olive oil, avocado oil, camellia oil, macadamia nut oil, evening primrose oil, jojoba oil, rapeseed oil, yolk oil, sesame oil, castor oil, safflower oil, cottonseed oil, soybean oil, tea seed oil, rice bran oil, germ oil, peanut oil, sunflower oil, almond oil, and corn oil; hydrocarbon oils such as squalane, liquid paraffin, and polybutene; ester oils such as isocetyl isostearate, ethylene glycol di-2-ethylhexanoate, cetyl 2-ethylhexanoate, trimethylolpropane tri-2-ethylhexanoate, pentaerythritol tetra-2-ethylhexanoate, glyceryl tri-2-heptylundecanoate, diisobutyl adipate, 2-hexyldecyl sebacate, glyceryl trioctanoate, glyceryl triisopalmitate, diisostearyl malate, isopropyl myristate, 2-octyldodecyl oleate, hexyldecyl dimethyloctanoate, 2-hexyldecyl myristate, myristyl myristate, octyldodecyl myristate, isopropyl palmitate, 2-ethylhexyl palmitate, 2-hexyldecyl palmitate, 2-heptylundecyl palmitate, butyl stearate, isocetyl stearate, decyl oleate, dodecyl oleate, oleyl oleate, myristyl lactate, cetyl lactate, cholesteryl 12-hydroxystearate, castor oil fatty acid methyl ester, 2-ethylhexyl succinate, 2-hexyldecyl adipate, di-2-heptylundecyl adipate, diisopropyl sebacate, di-2-ethylhexyl sebacate, neopentylglycol dicaprate, neopentylglycol dioctanoate, glyceryl tri-2-ethylhexanoate, glyceryl trimyristate, glyceryl tri-2-heptylundecanoate, and trimethylolpropane triisostearate; linear silicone oils such as dimethylpolysiloxane and methylphenylpolysiloxane; cyclic silicone oils such as octamethylcyclotetrasiloxane and decamethylcyclopentasiloxane; triglycerin; and fluorinated oils. One or more kinds of these liquid oils can be used. An amount of liquid oils, which is not restricted to, is usually 20 mass % to 70 mass % of the entire cosmetic.

In the stick-shaped solid cosmetic of the present invention, if needed, in addition to the above-mentioned ingredients, other ingredients normally used in a cosmetic or a medical external composition for skin can be used, within a range which does not deteriorate the effect of the present invention. Examples thereof include powders, surfactants, humectants, water-soluble polymers, thickeners, film-forming agents, ultraviolet absorbing agents, metal ion sequestering agents, lower alcohols, multivalent alcohols, sugars, amino acids, organic amines, polymer emulsions, pH adjusting agents, skin nutrients, whitening agents, anti-inflammatory agents, vitamins, antioxidants, antioxidant aids, antiseptics, perfumes, and water.

Examples of powders include silicic anhydride, hydrophobized silicic anhydride, inorganic powders (e.g., talc, kaolin, mica, sericite, muscovite, phlogopite, synthetic mica, red mica, biotite, vermiculite, magnesium carbonate, calcium carbonate, aluminum silicate, barium silicate, calcium silicate, magnesium silicate, strontium silicate, tungsten acid metal salt, magnesium, silica, zeolite, barium sulfate, calcinated calcium sulfate (calcined gypsum), calcium phosphate, fluorine apatite, hydroxyapatite, ceramic powder, metal soap (e.g., zinc myristate, calcium palmitate, aluminium stearate), boron nitride and the like); organic powders (e.g., polyamide resin powder (nylon powder), polyethylene powder, methyl polymethacrylate powder, polystyrene powder, resin powder of copolymer of styrene and acrylic acid, benzoguanamine resin powder, polyethylene tetrafluoride powder, cellulose powder and the like); inorganic white pigments (e.g., titanium dioxide, zinc oxide and the like); inorganic red series pigments (e.g., iron oxide (red iron oxide), iron titanate and the like); inorganic brown series pigments (e.g., γ-iron oxide and the like); inorganic yellow series pigments (e.g., yellow iron oxide, loess and the like); inorganic black series pigments (e.g., black iron oxide, lower titanium oxide and the like); inorganic purple series pigments (e.g., mangoviolet, cobalt-violet and the like); inorganic green series pigments (e.g., chromium oxide, chromium hydroxide, cobalt titanate and the like); inorganic blue series pigments (e.g., ultramarine, Prussian blue and the like); pearl pigments (e.g., titanium oxide-coated mica, titanium oxide-coated bismuth oxychloride, titanium oxide-coated talc, colored titanium oxide-coated mica, bismuth oxychloride, fish scale foil and the like); metal powder pigments (e.g., aluminum powder, copper powder and the like); organic pigments such as zirconium, barium or aluminum lake and the like (e.g., organic pigments such as Red No.201, Red No.202, Red No.204, Red No.205, Red No.220, Red No.226, Red No.228, Red No.405, Orange No.203, Orange No.204, Yellow No.205, Yellow No.401 and Blue No.404, Red No.3, Red No.104, Red No.106, Red No.227, Red No.230, Red No.401, Red No.505, Orange No.205, Yellow No.4, Yellow No.5, Yellow No.202, Yellow No.203, Green No.3, and Blue No.1 and the like); and natural colorants (e.g., chlorophyll, β-carotene and the like).

The stick-shaped solid cosmetic of the present invention can be applied to a lipstick, a lip cream, an eyeshadow, a cheek color, a foundation, a concealer, and the like. These cosmetics may be colorless or colored.

The present invention will hereinafter be described in further detail by examples. However, the present invention is not limited thereto. The blending amount is expressed in the mass % with respect to the entire composition unless otherwise noted.

EXAMPLE 1

(Conditions for the Measurement of Penetration Hardness)

Samples stored at 25° C. were measured with a FUDOH rheometer (Rheotech Co., Ltd.) under the conditions of the penetrator diameter of 1 mm, penetration of 3 mm, and the rise velocity of 2 cm/min. The penetration hardness is shown with the measured maximum stress value (force on the penetrator) at the penetration depth of 0 to 3 mm.

(Hardness Measurement of Stick-shaped Solid Cosmetics)

The hardness measurement for stick-shaped solid cosmetics was conducted in the following way. A stick-shaped solid cosmetic (sections outside the inner holder) is cut along a plane perpendicular to the central axis. Under the above-described hardness measurement conditions, a cylindrical penetrator is vertically (perpendicular to the cut surface) penetrated at the central axis of the cut surface. The measurement was conducted for the top portion, the middle portion, and the boundary portion of the stick-shaped solid cosmetic, respectively. Here, the "boundary portion" indicates the border located between the inner holder section and the section outside of the inner holder. The "top portion" indicates the section located at 10 mm from the tip of the stick-shaped solid cosmetic to the direction of the boundary portion. The "middle portion" indicates the section located at the ½ length, from the "top portion", of the axial length from the top portion of the stick-shaped solid cosmetic to the boundary portion.

In the following tests, approximately cylindrical stick-shaped solid cosmetics with the length from the tip to the boundary portion of 28 mm and the diameter at the boundary portion of 12.5 mm were used.

(Control Example)

The basic formulation of a conventional stick-shaped solid cosmetic is shown below.

| (Formulation) | (mass %) |
| --- | --- |
| (1) polyethylene wax | 4.0 |
| (2) microcrystalline wax | 1.0 |
| (3) ceresin | 5.0 |
| (4) candelilla wax | 3.0 |
| (5) polyisobutene | 20.0 |
| (6) petrolatum | 10.0 |
| (7) squalane | 10.0 |
| (8) diisostearyl malate | 10.0 |
| (9) diglyceryl triisostearate | 10.0 |
| (10) glyceryl trioctanoate | 23.7 |
| (11) Red No. 202 | 0.1 |
| (12) titanium dioxide | 1.2 |
| (13) iron oxide (red) | 1.5 |
| (14) iron oxide (yellow) | 0.5 |
| (15) antioxidant | Q.S. |
| (16) perfume | Q.S. |

(Preparation Method)

Ingredients (1) to (16) were heated to 95° C., and the melted, stirred, and mixed material was poured into a stick-shaped mold and then cooled.

In the above-described conventional stick-shaped cosmetic (Control Example), the hardness of the top portion was 0.40 N, the hardness of the middle portion was 0.40 N, and the hardness of the boundary portion was 0.40 N; thus the cosmetic had approximately a constant high hardness from the top portion to the boundary portion.

The above-described conventional stick-shaped cosmetic (Control Example) had high breakage strength during use; however, a smooth feeling in use could not be achieved. Therefore, a soft stick-shaped cosmetic (Comparative Example) was produced, and tests were conducted concerning the below-described items to compare with the Control Example.

COMPARATIVE EXAMPLE

| (Formulation) | (mass %) |
|---|---|
| (1) polyethylene wax | 0.0 |
| (2) microcrystalline wax | 1.0 |
| (3) ceresin | 5.0 |
| (4) candelilla wax | 3.0 |
| (5) polyisobutene | 20.0 |
| (6) petrolatum | 10.0 |
| (7) squalane | 10.0 |
| (8) diisostearyl malate | 10.0 |
| (9) diglyceryl triisostearate | 10.0 |
| (10) glyceryl trioctanoate | 26.7 |
| (11) Red No. 202 | 0.1 |
| (12) titanium dioxide | 1.2 |
| (13) iron oxide(red) | 1.5 |
| (14) iron oxide(yellow) | 0.5 |
| (15) antioxidant | Q.S. |
| (16) perfume | Q.S. |

(Preparation Method)

Ingredients (1) to (16) were heated to 95° C., and the melted, stirred, and mixed material was poured into a stick-shaped mold and then cooled.

In the above-described stick-shaped cosmetic (Comparative Example), the hardness of the top portion was 0.18 N, the hardness of the middle portion was 0.18 N, and the hardness of the boundary portion was 0.18 N; thus the cosmetic had approximately a constant low hardness from the top portion to the boundary portion.

(I) Product Strength

The breakage of samples stored at 25° C. was tested during actual use by 20 professional panelists and evaluated based on the following criteria.

○: Breakage was not observed.
Δ: 1 to 4 panelists out of 20 panelists experienced breakage.
X: 5 panelists or more out of 20 panelists experienced breakage.

(II) Smoothness

A sensory test, of samples stored at 25° C., was conducted concerning the smoothness during actual use (the control example was set at ±0 as a standard) by 20 professional panelists based on the following criteria, and then the average score was calculated.

+2: smooth feeling
+1: somewhat smooth feeling
±0: borderline
−1: not too smooth feeling
−2: no smooth feeling The results are shown in Table 1.

TABLE 1

|  | Control Ex. (hardness: 0.40N) | Comparative Ex. (hardness: 0.18N) |
|---|---|---|
| (I) Product strength | ○ | X |
| (II) Smoothness | −0.7 | 1.3 |

The feeling in use of the soft stick-shaped cosmetics (Comparative Example) was smoother than that of the conventional hard stick-shaped cosmetic (Control Example); however, it was easily breakable and the shape-retaining ability necessary for the product could not be obtained. On the other hand, the conventional hard stick-shaped cosmetic (Control Example) had satisfactory product strength; however, the feeling in use was not smooth.

Next, a stick-shaped cosmetic was produced according to the following formulation using two phases, namely, Phase A and Phase B with different hardness.

| | (mass %) | |
|---|---|---|
| (Formulation) | Phase A | Phase B |
| (1) polyethylene wax | 0.0 | 4.0 |
| (2) microcrystalline wax | 1.0 | 1.0 |
| (3) ceresin | 5.0 | 5.0 |
| (4) candelilla wax | 3.0 | 3.0 |
| (5) polyisobutene | 20.0 | 20.0 |
| (6) petrolatum | 10.0 | 10.0 |
| (7) squalane | 10.0 | 10.0 |
| (8) diisostearyl malate | 10.0 | 10.0 |
| (9) diglyceryl triisostearate | 10.0 | 10.0 |
| (10) glyceryl trioctanoate | 26.7 | 23.7 |
| (11) Red No. 202 | 0.1 | 0.1 |
| (12) titanium dioxide | 1.2 | 1.2 |
| (13) iron oxide(red) | 1.5 | 1.5 |
| (14) iron oxide(yellow) | 0.5 | 0.5 |
| (15) antioxidant | Q.S. | Q.S. |
| (16) perfume | Q.S. | Q.S. |

(Preparation Method)

The ingredients (1) to (16) of Phase A and those of Phase B were separately heated at 95° C., and they were melted, stirred, and mixed.

The above heat-melted Phase A and Phase B were poured into a stick-shaped mold while being mixed. The filling of Phase A was completed sooner, and only Phase B was poured after that. Then the material was solidified by cooling.

The hardness of the top portion of this stick-shaped cosmetic was 0.20 N, the hardness of the middle portion was 0.27 N, and the hardness of the boundary portion was 0.36 N. Thus, the hardness gradually increased from the top portion to the boundary portion.

The product strength and the smoothness were evaluated for the above two-phase type stick-shaped cosmetic based on the above evaluation criteria, and the feeling in use was evaluated based on the following evaluation criteria.

(III) Feeling in Use

The stick-shaped cosmetic was cut at the middle portion located between the top portion and the boundary portion, and the sample without the upper part was stored at 25° C. Then the sensory test, by 20 professional panelists, was conducted if there is any uncomfortable feeling, during actual use, due to the hardness difference between Phase A and Phase B (the control example was set at +0 as a standard) based on the following criteria, and the average score was calculated.

+0: comfortable
−1: somewhat uncomfortable
−2: uncomfortable

The test results are shown below.

(I) Product strength: ○
(II) Smoothness: 1.4
(III) Uncomfortable feeling: 0

The above two-phase type stick-shaped cosmetic gave smooth feeling in use, it was not easily breakable, and it had satisfactory shape-retaining ability. In addition, there was no uncomfortable feeling during use.

Thus, it was confirmed that a stick-shaped cosmetic with smooth feeling in use and excellent product strength could be obtained by producing a stick-shaped solid cosmetic that has increasing hardness from the top portion to the direction of the boundary portion by combining compositions of different hardness.

EXAMPLE 2

Based on the above-described production method, compositions with various hardness were prepared, and the preferable hardness and the preferable hardness difference were investigated. The hardness for Phase A and Phase B is the hardness before the stick-shaped solid cosmetic is molded.

TABLE 2

|  | Test Examples | | | |
|---|---|---|---|---|
|  | 1-1 | 1-2 | 1-3 | 1-4 |
| Hardness of phase A (N) | 0.02 | 0.05 | 0.10 | 0.15 |
| Hardness of phase B (N) | 0.25 | 0.25 | 0.30 | 0.35 |
| Hardness difference between Phase A and B (N) | 0.23 | 0.20 | 0.20 | 0.20 |
| Hardness of top portion (N) | 0.06 | 0.07 | 0.14 | 0.21 |
| Hardness of middle portion (N) | 0.13 | 0.15 | 0.20 | 0.24 |
| Hardness of boundary portion (N) | 0.21 | 0.23 | 0.27 | 0.31 |
| Hardness difference between top and boundary portion ΔN (N) | 0.15 | 0.16 | 0.13 | 0.10 |
| Hardness difference between top and middle portion ΔN' (N) | 0.07 | 0.08 | 0.06 | 0.03 |
| ΔN'/ΔN | 47% | 50% | 46% | 30% |
| (I)Product strength | X | Δ | ○ | ○ |
| (II)Smoothness | 2.0 | 1.8 | 1.6 | 1.4 |
| (III)Uncomfortable feeling | 0 | 0 | 0 | 0 |

TABLE 3

|  | Test Examples | | |
|---|---|---|---|
|  | 1-5 | 1-6 | 1-7 |
| Hardness of phase A (N) | 0.25 | 0.30 | 0.35 |
| Hardness of phase B (N) | 0.45 | 0.50 | 0.55 |
| Hardness difference between Phase A and B (N) | 0.20 | 0.20 | 0.20 |
| Hardness of top portion (N) | 0.30 | 0.35 | 0.38 |
| Hardness of middle portion (N) | 0.34 | 0.39 | 0.44 |
| Hardness of boundary portion (N) | 0.41 | 0.46 | 0.51 |
| Hardness difference between top and boundary portion ΔN (N) | 0.11 | 0.11 | 0.13 |
| Hardness difference between top and middle portion ΔN' (N) | 0.04 | 0.04 | 0.06 |
| ΔN'/ΔN | 36% | 36% | 46% |
| (I)Product strength | ○ | ○ | ○ |
| (II)Smoothness | 1.1 | 0.8 | 0.2 |
| (III)Uncomfortable feeling | 0 | 0 | 0 |

TABLE 4

|  | Test Examples | | | |
|---|---|---|---|---|
|  | 1-8 | 1-9 | 1-10 | 1-11 |
| Hardness of phase A (N) | 0.15 | 0.15 | 0.15 | 0.15 |
| Hardness of phase B (N) | 0.16 | 0.20 | 0.25 | 0.55 |
| Hardness difference between Phase A and B (N) | 0.01 | 0.05 | 0.10 | 0.40 |
| Hardness of top portion (N) | 0.15 | 0.16 | 0.17 | 0.25 |
| Hardness of middle portion (N) | 0.15 | 0.18 | 0.20 | 0.33 |

TABLE 4-continued

|  | Test Examples | | | |
|---|---|---|---|---|
|  | 1-8 | 1-9 | 1-10 | 1-11 |
| Hardness of boundary portion (N) | 0.16 | 0.19 | 0.22 | 0.49 |
| Hardness difference between top and boundary portion ΔN (N) | 0.01 | 0.03 | 0.05 | 0.24 |
| Hardness difference between top and middle portion ΔN' (N) | 0.00 | 0.02 | 0.03 | 0.08 |
| ΔN'/ΔN | 0% | 67% | 60% | 33% |
| (I)Product strength | X | Δ | ○ | ○ |
| (II)Smoothness | 1.3 | 1.2 | 1.3 | 1.2 |
| (III)Uncomfortable feeling | 0 | 0 | 0 | 0.2 |

TABLE 5

|  | Test Examples | |
|---|---|---|
|  | 1-12 | 1-13 |
| Hardness of phase A (N) | 0.15 | 0.15 |
| Hardness of phase B (N) | 0.65 | 0.75 |
| Hardness difference between Phase A and B (N) | 0.50 | 0.60 |
| Hardness of top portion (N) | 0.27 | 0.29 |
| Hardness of middle portion (N) | 0.38 | 0.42 |
| Hardness of boundary portion (N) | 0.58 | 0.63 |
| Hardness difference between top and boundary portion ΔN (N) | 0.31 | 0.34 |
| Hardness difference between top and middle portion ΔN' (N) | 0.11 | 0.13 |
| ΔN'/ΔN | 35% | 38% |
| (I)Product strength | ○ | ○ |
| (II)Smoothness | 1.0 | 0.9 |
| (III)Uncomfortable feeling | 1.0 | 1.6 |

From the results of Tables 2 to 5, it was found that the hardness of Phase A was preferably 0.05 N to 0.35 N, and more preferably 0.10 N to 0.25 N, and that the hardness difference between Phase A and Phase B was preferably 0.05 N to 0.50 N, and more preferably 0.10 N to 0.40 N.

Similarly, it was found that the hardness of the top portion of the stick-shaped solid cosmetic was preferably 0.07 N to 0.38 N, and more preferably 0.13 N to 0.35 N, and that the hardness difference between the top portion and the boundary portion was preferably 0.03 N to 0.31 N, and more preferably 0.09 N to 0.24 N. It was also found that the hardness difference ΔN' between the top portion and the middle portion was preferably 30% to 67% of the hardness difference ΔN between the top portion and the boundary portion, and more preferably 30% to 60%.

EXAMPLE 3

Stick-shaped solid cosmetics were produced using Phase A with the hardness of 0.15 N and Phase B with the hardness of 0.40 N, and the desirable volume ratio of the two phases was investigated.

TABLE 6

|  | Test Examples | | | | | |
|---|---|---|---|---|---|---|
|  | 2-1 | 2-2 | 2-3 | 2-4 | 2-5 | 2-6 |
| Ratio of Phase A (%) | 40 | 50 | 62 | 71 | 83 | 90 |
| Ratio of Phase B (%) | 60 | 50 | 38 | 29 | 17 | 10 |
| Phase B/Phase A | 1.5 | 1.0 | 0.6 | 0.4 | 0.2 | 0.1 |
| (I) Product strength | ○ | ○ | ○ | ○ | Δ | X |

From the results of Table 6, it was found that the volume ratio of Phase B to Phase A was preferably 0.2 or higher, and more preferably 0.4 to 1.5.

What is claimed is:

1. A stick-shaped solid cosmetic having a top portion and a bottom portion which is retained in a tubular inner holder, the solid cosmetic comprising a wax with a melting point of 45° C. or higher and a liquid oil component, wherein the hardness of the top portion is 0.07 N to 0.38 N, and the hardness of a boundary portion, which is a border between a retained portion in the inner holder and a portion outside of the inner holder, is 0.03 N to 0.31 N higher than the hardness of the top portion at least in the vicinity of a central axis of the stick-shaped solid cosmetic.

2. The stick-shaped solid cosmetic of claim 1, wherein at least in the vicinity of the central axis of the stick-shaped solid cosmetic, the hardness gradually increases from the top portion to the boundary portion.

3. The stick-shaped solid cosmetic of claim 2, wherein the hardness at a location 8 mm from the boundary portion to a direction of the top portion is 0.15 N or higher, and wherein the hardness is at least 0.1 N higher than the hardness of the top portion.

4. The stick-shaped solid cosmetic of claim 2, wherein at least in the vicinity of the central axis of the stick-shaped solid cosmetic, the hardness of a middle portion, which is located between the top portion and the boundary portion, is not less than the hardness of the top portion and not more than the hardness of the boundary portion, and hardness difference between the top portion and the middle portion is 30% to 67% of hardness difference between the top portion and the boundary portion.

5. The stick-shaped solid cosmetic of claim 4, wherein the hardness at a location 8 mm from the boundary portion to a direction of the top portion is 0.15 N or higher, and wherein the hardness is at least 0.1 N higher than the hardness of the top portion.

6. The stick-shaped solid cosmetic of claim 1, wherein the hardness at a location 8 mm from the boundary portion to a direction of the top portion is 0.15 N or higher, and wherein the hardness is at least 0.1 N higher than the hardness of the top portion.

7. A method of producing a stick-shaped solid cosmetic, comprising the steps of:
   (a) separately heating and melting Phase A, wherein Phase A comprises a liquid oil component and a wax with a melting point of 45° C. or higher, and has a hardness of 0.05 N to 0.35 N;
   (b) separately heating and melting at least one Phase B, wherein Phase B comprises a liquid oil component and a wax with a melting point of 45° C. or higher, and wherein the hardness of Phase B is 0.05 N to 0.50 N higher than that of Phase A;
   (c) filling the heat-melted Phase A and the heat-melted Phase B into a mold while being mixed, wherein the filling of Phase A into the mold is completed sooner than the filling of Phase B into the mold; and
   (d) solidifying the mixture filled into the mold by cooling, to produce a stick-shaped solid cosmetic in which hardness gradually increases from a top portion to a bottom portion.

8. The method of claim 7, wherein a the volume ratio of Phase B to Phase A is 0.2 or higher.

* * * * *